United States Patent
Puttilli et al.

(10) Patent No.: US 10,750,971 B2
(45) Date of Patent: Aug. 25, 2020

(54) DEVICE FOR RECORDING VIDEO-ELECTROENCEPHALOGRAMS

(71) Applicant: AB Medica S.p.A., Milan MI (IT)

(72) Inventors: Cosimo Damiano Puttilli, Milan (IT); Mauro Picciafuoco, Milan MI (IT); Pantaleo Romanelli, Milan MI (IT)

(73) Assignee: AB MEDICA S.P.A., Milan (IT)

(*) Notice: Subject to any disclaimer, the term of this patent is extended or adjusted under 35 U.S.C. 154(b) by 305 days.

(21) Appl. No.: 15/761,198

(22) PCT Filed: Sep. 28, 2016

(86) PCT No.: PCT/EP2016/073121
§ 371 (c)(1),
(2) Date: Mar. 19, 2018

(87) PCT Pub. No.: WO2017/055354
PCT Pub. Date: Apr. 6, 2017

(65) Prior Publication Data
US 2018/0263523 A1  Sep. 20, 2018

(30) Foreign Application Priority Data

Sep. 30, 2015 (IT) .......................... 102015000056995

(51) Int. Cl.
*A61B 5/0476* (2006.01)
*A61B 5/00* (2006.01)

(52) U.S. Cl.
CPC .......... *A61B 5/0476* (2013.01); *A61B 5/0077* (2013.01); *A61B 5/4094* (2013.01);
(Continued)

(58) Field of Classification Search
CPC .... A61B 5/0476–04847; A61B 5/6835; A61B 5/0077; A61B 5/6803
See application file for complete search history.

(56) References Cited

U.S. PATENT DOCUMENTS

| | | |
|---|---|---|
| 5,038,782 A | 8/1991 | Gevins et al. |
| 2011/0046502 A1 | 2/2011 | Pradeep et al. |

(Continued)

FOREIGN PATENT DOCUMENTS

| | | |
|---|---|---|
| CN | 202798941 | 3/2013 |
| EP | 2762069 A1 | 8/2014 |
| WO | 2013142316 A1 | 9/2013 |

OTHER PUBLICATIONS

International Search Report and Written Opinion for International Application No. PCT/EP2016/073121 (9 Pages) (dated Dec. 14, 2016).

*Primary Examiner* — Meredith Weare
(74) *Attorney, Agent, or Firm* — Lucas & Mercanti, LLP

(57) ABSTRACT

The invention relates to a portable device for video electro-encephalography. The device has a central portion to which a plurality of arcuate arms are directly or indirectly connected in a movable manner. The arms together define a helmet structure adapted to be worn on the head of a patient, arm is configured to allow mounting of one or more electrodes which are connected to an electronic central unit mounted on the helmet structure. The device also has a supporting member and a video camera mounted on the supporting member so as to face the helmet structure, said video camera. The arms have a first arm and a second arm which extend away from each other in a longitudinal direction (L), as well as a third arm and a fourth arm which extend away from each other in a front direction (F). The first and second arms are pivoted on the central portion about respective axes parallel to the front direction (F), and the third and fourth arms are pivoted about respective axes parallel to the longitudinal direction (L).

19 Claims, 6 Drawing Sheets

(52) U.S. Cl.
CPC .......... *A61B 5/6803* (2013.01); *A61B 5/6835* (2013.01); *A61B 2562/04* (2013.01)

(56) References Cited

U.S. PATENT DOCUMENTS

| | | |
|---|---|---|
| 2011/0237923 A1 | 9/2011 | Picht et al. |
| 2012/0143020 A1 | 6/2012 | Bordoley et al. |
| 2014/0051044 A1 | 2/2014 | Badower et al. |
| 2015/0112153 A1* | 4/2015 | Nahum ................ A61B 5/6803 600/301 |
| 2016/0360990 A1* | 12/2016 | Altshuler ............. A61B 5/0478 |

* cited by examiner

DEVICE FOR RECORDING VIDEO-ELECTROENCEPHALOGRAMS

CROSS-REFERENCE TO RELATED APPLICATIONS

This application is a 371 of PCT/EP2016/073121, filed Sep. 28, 2016 which claims the benefit of Italian Patent Application No. 102015000056995, filed Sep. 30, 2015.

FIELD OF THE INVENTION

The present invention generally relates to devices for the acquisition and recording of electroencephalograms and in particular to a portable, wireless device for video electroencephalography configured as a helmet that can be worn on the head of a patient.

BACKGROUND OF THE INVENTION

Electroencephalography (EEG) is the recording of the electrical activity of the brain by detecting, i.e. acquiring, the electric potential associated with the currents flowing on the cerebral cortex. Electroencephalography is a non-invasive investigation means having a fundamental importance for the study of the physiology and pathophysiology of nervous centers. EEG is very useful in the differential diagnosis between epileptic and non-epileptic seizures and contributes to the definition of the nature of the crisis and/or epileptic syndrome.

It is known that the registration of a electroencephalographic signal is carried out by applying at different points of the head of a patient two or more electrodes, a "bias" electrode, as well as a reference electrode. These electrodes are held together e.g. by way of an elastic cap and are applied on the scalp of the patient at pre-established positions according to different standards. The standard positioning system known as "International System 10/20" is particularly widespread due to its simplicity of use and effectiveness. The "International System 10/20" exploits as skull landmarks the craniometric point "inion", i.e. the most prominent point at the back of the head, and the craniometric point "nasion", i.e. where the top of the nose meets the ridge of the forehead. According to this standard, frontal polar electrodes are placed above the eyebrows at the 10% of the inion-nasion distance, frontal electrodes are placed on the same line of the frontal polar electrodes but at the 20% of the inion-nasion distance, and, with respect to the latter, central, parietal and occipital electrodes are positioned at a respective distance progressively greater than 20%.

Electroencephalography applications are numerous and include the study of sleeping disorders such as apnea, dyssomnia (insomnia, hypersomnia, narcolepsy) and parasomnia (bruxism, bedwetting, night terror, sleep walking), detection of brain death, which is characterized by a flat EEG record, and detection of alterations caused by abscesses, calcifications, cysts, hematomas, bleeding, inflammation, malformations or benign or malignant tumors of the brain.

Electroencephalography is employed as an aid in the diagnosis of senile dementia and neurodegenerative diseases such as Parkinson's disease and Alzheimer's disease. It also represents a monitoring tool for the neuromotor apparatus in the evaluation of cognitive and motor recovery at the level of the central nervous system.

Electroencephalography is increasingly being used in the diagnosis and monitoring of seizure disorders such as epilepsy.

Epilepsy is a chronic neurological disorder that affects millions of people worldwide. It is characterized by recurrent seizures caused by abnormal activity of brain nerve cells. Seizures can occur as attention loss, fainting, convulsion and, when they are frequent there is a risk of personal injury up to death. An accurate diagnosis of epilepsy is crucial and requires several tests, including electroencephalography, which is even considered necessary and indispensable.

EEG monitoring of patients with epilepsy are typically performed in hospitals and specialized centers by placing a patient on a bed and connecting individual electrodes placed on the patient's head to a fixed EEG device provided with data processing units through wires.

In order to carry out diagnoses and management of patients with suspected or already established epilepsy traditional electroencephalograms are typically recorded also known as "Standard EEG", as well as dynamic electroencephalograms of a longer duration, such as 24 hours, known as "Holter EEG" or "Ambulatory EEG".

Also known are the so-called "Video-EEG" monitoring systems, according to which an epileptic patient is video recorded for a short or a long time while subjected to an electroencephalographic monitoring. Video-EEG monitoring is carried out in a hospital in a specific hospital room equipped with a closed circuit television system configured for both the daytime and nighttime recording. There is an increasing scientific interest in Video-EEG systems, because they allow to correlate EEG records with actual images of a patient, thus making it possible to analyze clinical data (myoclonic events, avert eyes, absences and the like) related to abnormalities detected by the EEG and hence to make differential diagnoses between epileptic and non-epileptic episodes, to improve the definition of the specific epileptic syndrome, as well as to quantify the crisis anomalies and to study sleeping disorders. Thanks to the possibility of relate EEG and images of a patient, the time required for a diagnosis can be greatly reduced.

Traditional electroencephalography is a long and uncomfortable examination for a patient and particularly for a pediatric patient, because of the time required for the positioning and connection of the electrodes to the acquisition system, and due to the duration of the recordings, which is typically between 20 and 40 minutes, but can also be longer, for example of the order of days, in the case of epilepsy since it is substantially impossible to predict the onset of a crisis.

In the specific case of Video-EEG monitoring a patient must stay in a bed, sitting or lying thereon assisted by an attendant with the additional constraint of having to keep a position well-framed by the cameras.

For dynamic or long-term EEG monitoring EEG portable devices configured to be worn by a patient are also known. These devices are configured like helmets and are equipped with a plurality of electrodes typically arranged according to the international standard 10/20. These helmets comprise a plurality of interconnected portions whose relative position is adjustable depending on the size of the patient's head. Bioelectric signals acquired through the electrodes can be transmitted to an electronic unit associated with the EEG device, e.g. mounted on a portion of the helmet, or to a remote electronic unit connected to the EEG device through wires or in a wireless mode.

The electrodes may be of a wet type, according to which the electrical contact with a patient's scalp is obtained indirectly through a conductive gel, or of a dry type, according to which the electrical contact with a patient's scalp is direct and requires a slight compression of an electrode on the scalp so as to penetrate through the hair and ensure a proper detection of the bioelectric signals. Dry-type electrodes are typically provided with a plurality of contact arms that contact a portion of the scalp at several points and can thus ensure an adequate electrical contact because they fit more easily through the hair.

Dynamic monitoring with portable EEG devices (Holter EEG) is considered more effective than monitoring with fixed EEG equipment, because it allows to perform monitoring either in a hospital or at home, where a patient generally has a more natural and relaxed attitude, which increases the probability of recording seizures, or more in general occurrence of the disorders to be investigated within a given time period. EEG monitoring at home is also a much less expensive than hospitalization in a specialized center and is therefore more sustainable for the public health.

A portable EEG device of the aforementioned type comprising wet electrodes is e.g. disclosed in the patent publication EP 2762069 A1.

Dry electrodes for use in EEG devices are for example disclosed in the international publication WO 2013/142316 A1.

In both cases, the electrodes have elastically deformable structures and/or means suitable to facilitate their positioning on a patient's head and to minimize the physical pain they bring during prolonged monitoring periods.

Also known are Video-EEG systems comprising a portable EEG device combined with a camera system such as a web-cam connected to a computer, allowing to carry out video monitoring at home, although in a less accurate way compared to a video monitoring carried out by way of a hospital equipment.

An example of a Video-EEG system is disclosed by the patent publication US 2014/051044 A1, which corresponds to the preamble of the independent claim 1.

Despite the availability of many types of portable devices for electroencephalography and video electroencephalography, there still exists the need to find improved devices particularly aimed at long-term monitoring of patients suffering from epilepsy, as well as at epilepsy diagnoses, which is an object of the present invention. Said object is achieved with a portable device for video electroencephalography, whose main features are specified in the first claim, while other features are specified in the remaining claims.

SUMMARY OF THE INVENTION

An idea of solution underlying the present invention is to make a portable device for video electroencephalography comprising a cap-shaped or helmet structure that may be adjusted according to the size of a patient's head, wherein the structure comprises a plurality of electrodes positioned according to the international standard 10/20.

The helmet has an ergonomic structure comprising a fixed central portion and a plurality of movable arms that can be oriented and pre-adjusted by a skilled operator in order to allow electrodes mounted thereon to reach specific positions required for the acquisition according to the international standard 10/20. The electrodes are mounted slidably on respective arms along slots wherein suitable seats are formed, the seats being configured to allow to firmly lock the electrodes at a plurality of predetermined positions, for example corresponding to those of the standard 10/20.

Thanks to these features it is possible to perform a number of monitoring cycles of a same patient without the need to reconfigure the helmet, and also dynamic or long-term monitoring (Holter), for example over a period of 24 hours, preventing the risk of modifying the position of the electrodes relative to their predetermined contact points due to movements of the patient.

The helmet arms are urged towards one another, i.e. towards a patient's head when the device is used, by way of elastic means such as torsion springs. The provision of elastic means is advantageous because it allows to approach as much as possible the electrodes to the scalp for a good acquisition of EEG signals.

The device according to the invention also comprises at least one video camera mounted on a support of the helmet structure and arranged so as to face the helmet. The camera is configured for both daytime and nighttime recording in order to allow monitoring over periods of 24 hours or longer.

Thanks to these features it is possible to provide a portable device for Video-EEG that can be worn by a patient and does not require any external device or dedicated environment for video recording, with the related constraints and movement restrictions.

In other words, thanks to the inventive device it is possible to carry out Video-EEG monitoring without resorting to specialized hospitals structures that require specially equipped rooms and have long waiting times due to their small number. Similarly to portable EEG devices, the portable device for Video-EEG according to the invention can follow a patient during his/her normal activities without forcing him/her to stay in a bed or in a confined space, thus increasing the already known benefits of portable EEG devices.

Another advantage of the portable device for Video-EEG according to the invention is that it does not require any external synchronization system between the bioelectric signals and the images, since the captured images are directly sent to the same electronic control unit used to acquire and process the EEG signals, which is configured to associate and synchronize the EEG records with the images.

The device according to the invention may also advantageously include a microphone, for example associated with the camera, which allows to associate sound data to video recordings, which enhances the quality and completeness of the video-EEG monitoring and contributes to the accuracy of diagnoses based on such monitoring.

According to a preferred embodiment of the invention, the audio/video signals acquired are sent to an external portable electronic unit in a "wireless" mode along with the EEG signals acquired from the electrodes. The external electronic unit may be configured so as to directly process the data in real time or after their acquisition, or to be connected, e.g. in a wireless mode, to any external electronic processing system.

According to a further embodiment of the invention, in the case of registration of a potential epilepsy seizure the portable Video-EEG device is configured to mark the record and/or send it in real time to a physician together with the records of the time periods that precede and follow the epileptic seizure, the duration of which may be set according to specific needs.

It is also an idea underlying the invention to equip the device with a plurality of dry electrodes. The provision of dry electrodes, which are per se known in the field e.g. from US 2011/046502, is advantageous because it promotes long-term monitoring, which is particularly desirable with epileptic patients, because such electrodes are inherently clean thanks to the absence of a conductive gel, and because they may be sterilized and reused.

The dry electrodes of the device of the invention are configured so as to allow to have multiple contact points with the scalp in order to enhance acquisition of the EEG signals. Dry electrodes of this type are known e.g. from US 2011/237923 A1, wherein each electrode has a cylindrical body featuring an external thread and supporting at one end a sensor having a brush-like shape with contact pins protruding off the body. Dry electrodes of this type are also known from U.S. Pat. No. 5,038,782 A, wherein each electrode is formed from a flexible metal alloy into a shape with multiple metal fingers spanning from a mount and dimpled at the free end.

Each dry electrode of the device of the invention comprises a mount made of a conductive metal material and a plurality of arms extending therefrom radially outwards. The arms are made of a conductive metal material and are partially embedded in an annular-shaped matrix made of a resilient polymeric material. Each arm includes a resilient portion restrained to the mount and a rigid portion restrained to the resilient portion, as well as a rounded portion arranged at the free end of the rigid portion.

Thanks to these features the dry electrodes are elastically deformable both axially and laterally much more than those described in the above mentioned publication U.S. Pat. No. 5,038,782 A, which allows to ensure an improved ergonomic positioning thereof on a patient's scalp and thus a better acquisition of the EEG signal over extended periods of time.

BRIEF DESCRIPTION OF THE DRAWINGS

Further advantages and features of the portable device for video electroencephalography according to the present invention will become clear to those skilled in the art from the following detailed and non-limiting description of embodiments thereof, with reference to the accompanying drawings in which.

DETAILED DESCRIPTION OF THE INVENTION

Figure 1:
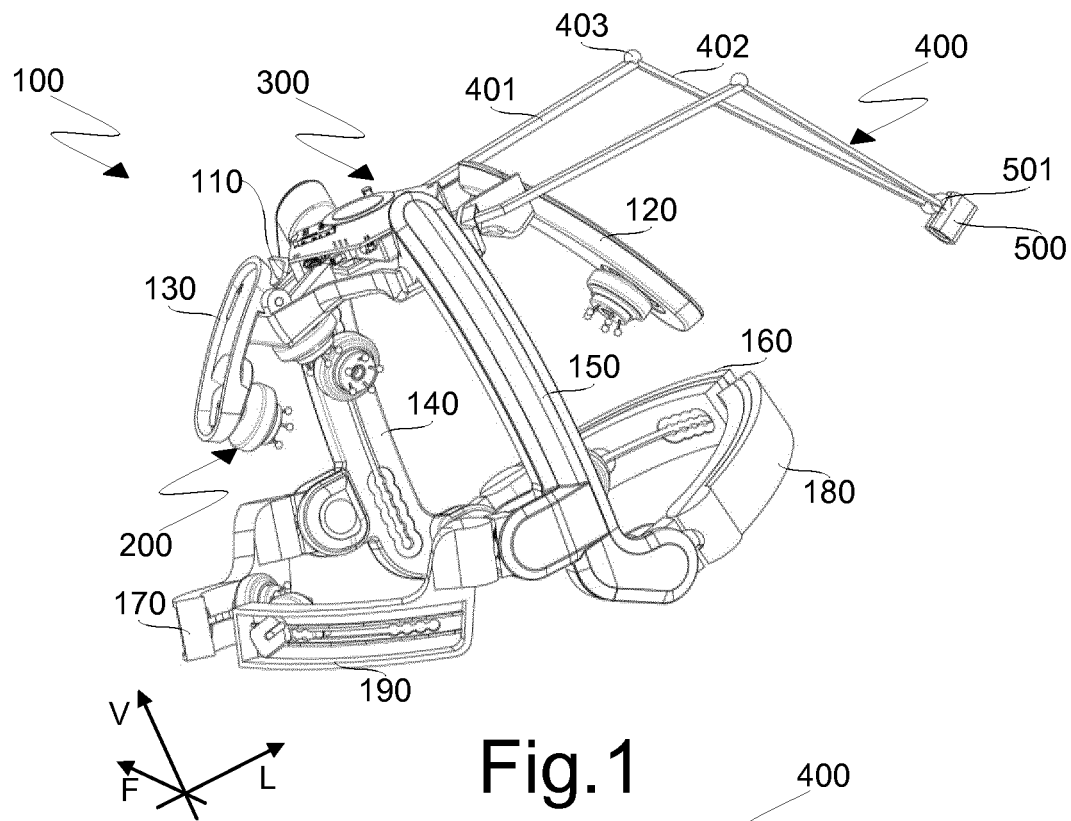
FIGS. 1 and 2 are perspective views showing a portable device for video electroencephalography according to the present invention from two different angles.
Figure 2:
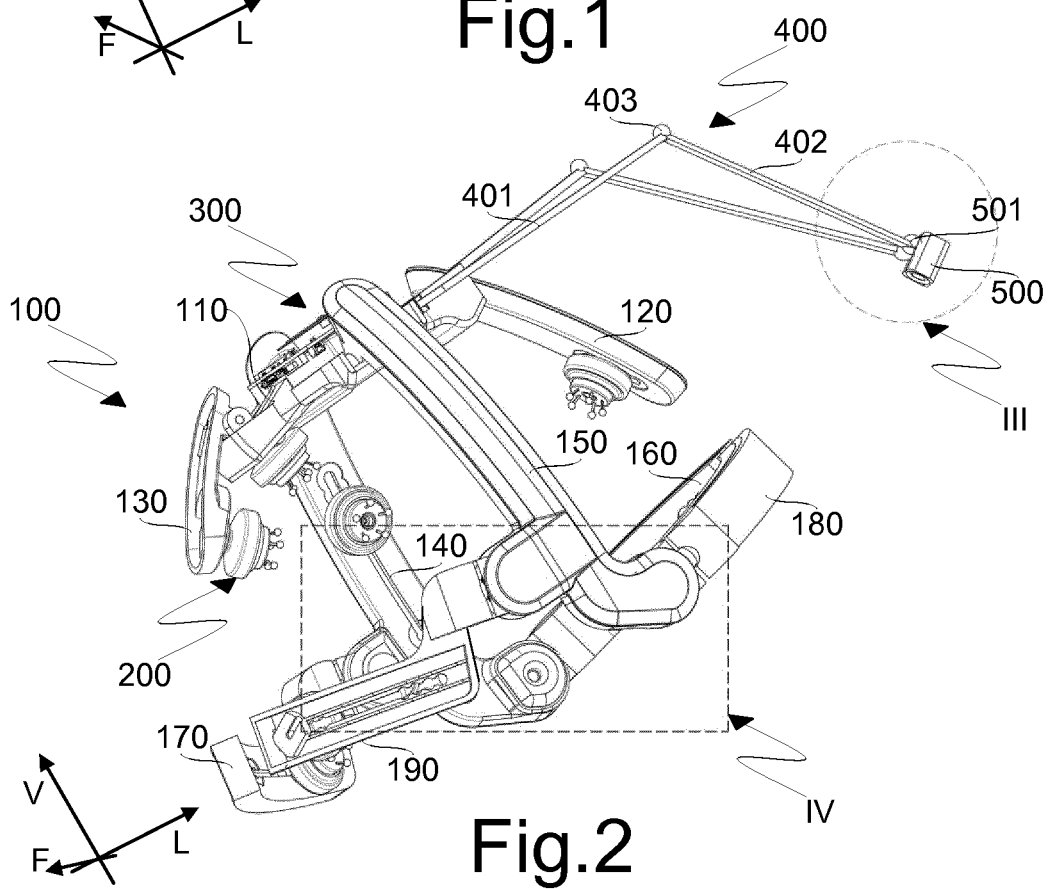
Figure 3:
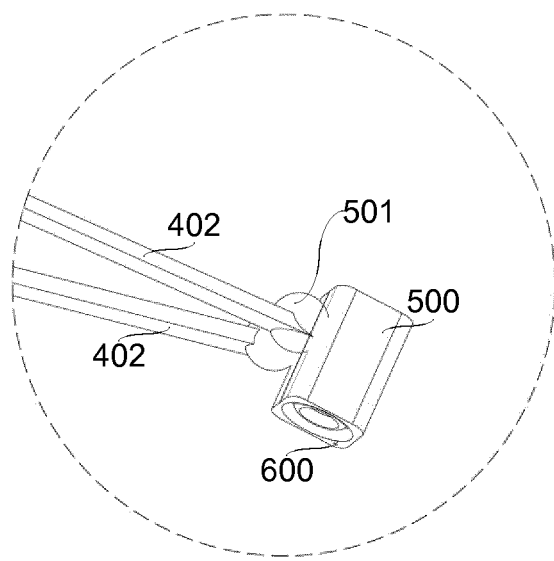
FIGS. 3 and 4 respectively show a detail III and a detail IV of FIG. 2.
Figure 4:
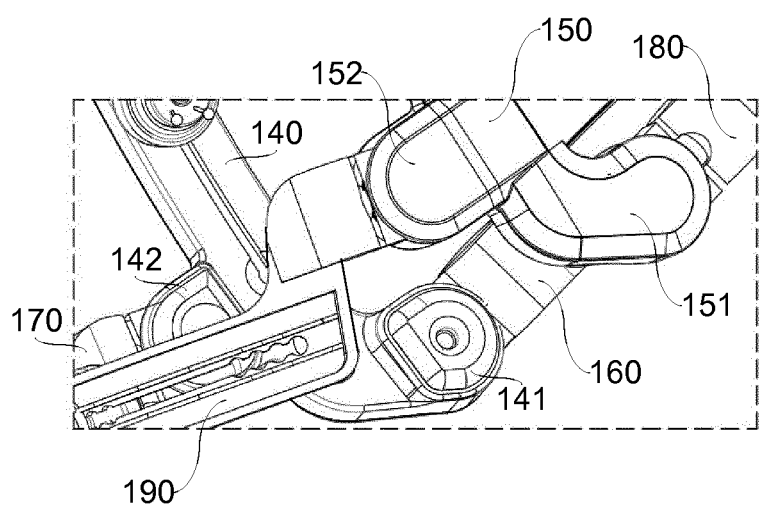

Referring to FIGS. 1 to 4, a portable device for EEG according to the invention is generally indicated by reference number 100 and is shown in a three dimensional reference system L, F, V, wherein in an operative condition of the device 100 a longitudinal direction L corresponds to the nasion-inion direction, or to a sagittal plane of a patient's body, a front direction F, perpendicular to the longitudinal direction L, represents a frontal or coronal plane of the patient's body, and a vertical direction V is perpendicular to the longitudinal direction L and the front direction F.

The device 100 comprises a central portion 110 to which, as it will be described in greater detail below, a plurality of arcuate shaped arms are connected in a movable manner, directly or indirectly. The arms and the central portion together define a helmet structure adapted to be worn on the head of a patient. Each arm is configured to receive one or more electrodes electrically connected to a central electronic unit mounted on the helmet structure.

In particular, a first arm 120 and a second arm 130 extend in opposite directions in the longitudinal direction L, while a third arm 140 and a fourth arm 150 extend in opposite directions in the front direction F. In an operative condition, the first arm 120 is intended to face the craniometric point nasion, while the second arm is intended to face the craniometric point inion.

The first and second arms 120, 130 are pivoted on the central portion 110 about respective axes parallel to the front direction F and can therefore be rotated with respect to the central portion 110 on a sagittal plane. The third and fourth arms 140, 150 are pivoted about respective axes parallel to the longitudinal direction L and can therefore be rotated with respect to the central portion 110 on a frontal plane.

As mentioned above, the arms 120, 130, 140, 150 of the device 100 all have an arcuate shape and define together with the central portion a helmet structure adapted to be fitted on the head of a patient. In the light of the kinematic constraints described above, it will be appreciated that such a helmet structure is adjustable depending on the size of the patient's head.

According to an embodiment of the invention, the device 100 may include biasing means (not shown) associated to the axes about which the arms 120, 130, 140, 150 pivoted on the central portion 110 rotate, for example torsion springs. The biasing means are configured to urge toward one another the arms that are mutually opposite with respect to the central portion 110 so as to allow the helmet to be closed on the head of a patient and thus to facilitate the contact between the electrodes and the scalp.

The device 100 also comprises a fifth arm 160 and a sixth arm 170, which are respectively restrained to the free end of the third arm 140 and extend in opposite directions in the longitudinal direction L, as well as a seventh arm 180 and an eighth arm 190, which are restrained to the free end of the fourth arm 150 and extend in opposite directions in the longitudinal direction L.

In the illustrated embodiment, the fifth and the sixth arms 160, 170 and the seventh and the eighth arms 180, 190 are e.g. restrained to appendices 141, 142 and 151, 152 of the third arm 140 and fourth arm 150, respectively.

More particularly, the fifth and the sixth arms 160, 170 and the seventh and eighth arms 180, 190 are respectively pivoted on the third arm 140 and fourth arm 150 about axes parallel to the front direction F, whereby they may be rotated relative to the third and fourth arms 140, 150 in the sagittal plane.

In order to ensure maintenance of a desired position of the fifth, sixth, seventh and eighth arms 160, 170, 180 and 190, clutch mechanisms with possible locking indentations may e.g. be used.

The fifth and the sixth arms 160, 170 and the seventh and eighth arms 180, 190 have respective arcuate shapes that extend from the ends 140 of the third arm and the fourth arm 150 towards the first and second arms 120, 130, thus completing the cap-shaped or helmet structure of the device 100.

Figure 5:
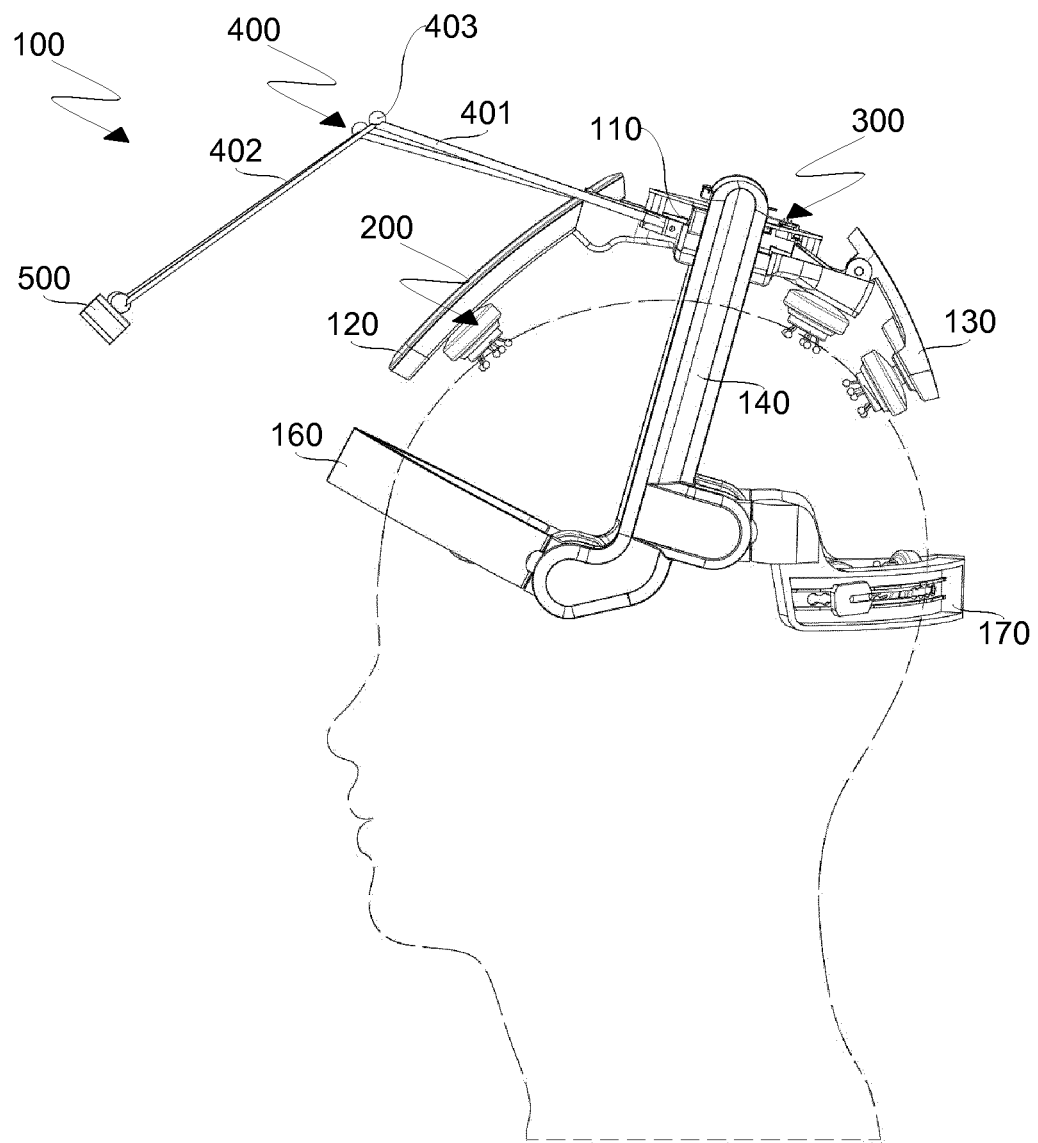
FIG. 5 is a side view schematically showing the portable device for video electroencephalography according to the present invention mounted on the head of a patient.
Figure 6:
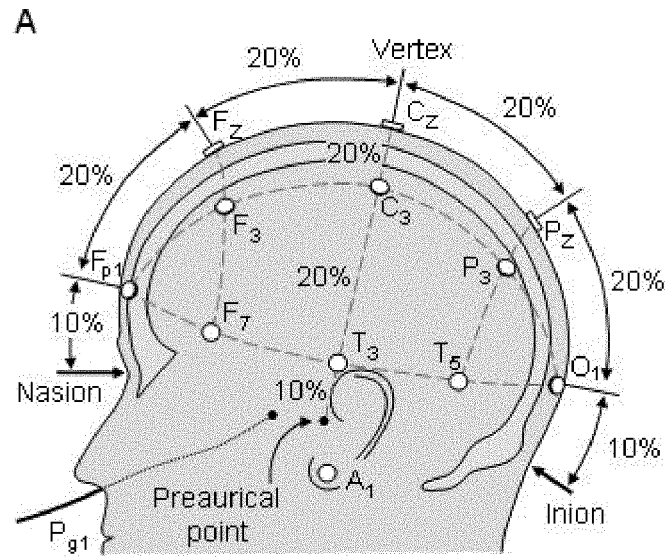
FIGS. 6 and 7 are respectively a side view and a top plan view that schematically show the positions of the electrodes of the device on the head of a patient according to the international standard 10/20.
Figure 7:
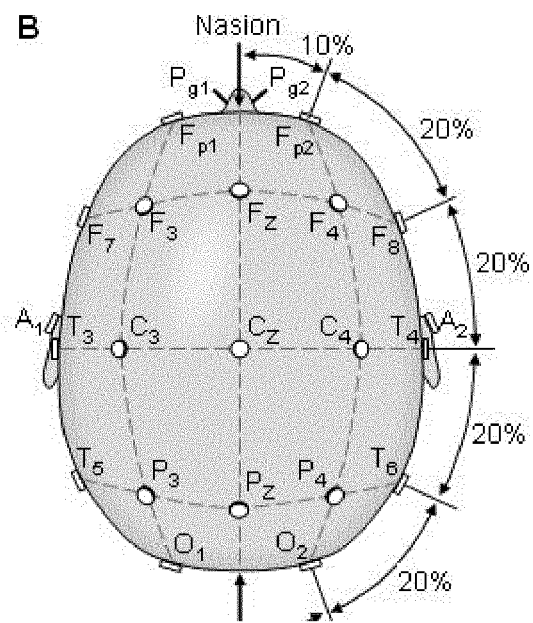

As shown in FIG. 5, the configuration of the device is such that, when mounted on the head of a patient, the first, fifth and seventh arms 120, 160 and 180 respectively extend from the head vertex and the temples towards the forehead (nasion direction), while the second, sixth and eighth arms 130, 170, 190 respectively extend from the head vertex and the temples towards the nape (inion direction). The third and the fourth arms 140, 150 instead extend from the head vertex towards the ears. In the side view of FIG. 5 only the central portion 110, the first and second arms 120, 130, the third arm 140 and the fifth and sixth arms 160, 170 restrained thereto may be seen.

The third and fourth arms 140, 150, the fifth and sixth arms 160, 170, and the seventh and eighth arms 180, 190 have the same shape and size two by two, so that the helmet structure of the device 100 is symmetric with respect to a sagittal plane.

Each arm is configured for the mounting of one or more electrodes 200 of the EEG device. The electrodes of the portable EEG device according to the invention are dry electrodes providing the advantage of being not subject to fouling from conductive gels and of not causing pain to a patient over prolonged monitoring periods, as well as of being able to be individually sterilized and reused.

In the illustrated embodiment the device 100 e.g. comprises ten electrodes. With reference to FIGS. 1, 2 and 6, 7, a first electrode is for example mounted under the central portion 110 so as to contact the head vertex in the position Cz of the 10/20 standard. A second electrode is mounted on the second arm 130 and acts for example as a bias electrode, while on the first arm 120 a third electrode is mounted e.g. in order to contact the Fz position of the 10/20 standard. A fourth electrode that e.g. acts as reference electrode is mounted between the electrodes intended to contact the Cz and Fz positions. Additional electrodes are arranged on the arms 140, 150 intended to contact the patient's temples, on the arms 160, 180 intended to contact the patient's forehead and on the arms 170, 190 intended to contact the patient's neck, hence reaching the positions $C_3$ and $C_4$, $F_{p1}$, $F_{p2}$ and $O_1$ and $O_2$ of the 10/20 standard.

Figure 8:
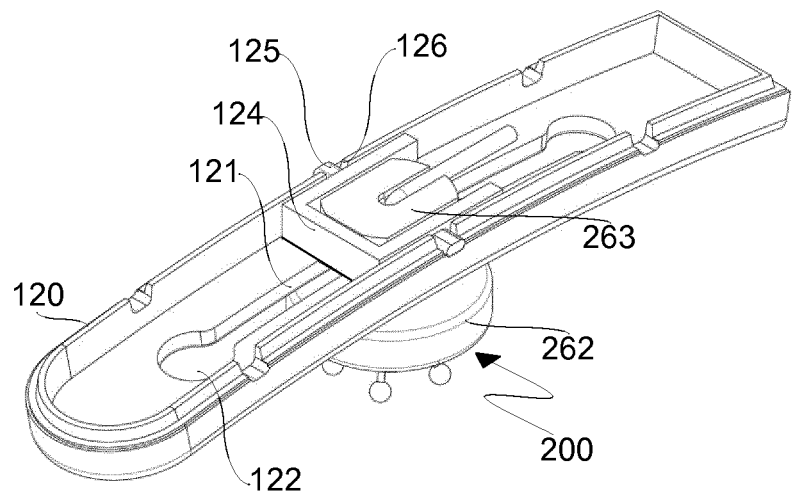
FIG. 8 is a perspective view showing a portion of one of the arms of the device and an electrode slidably mounted in the arm.
Figure 9:
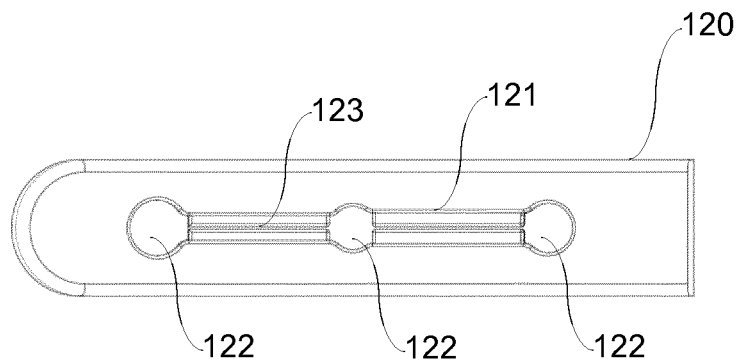
FIG. 9 is a plan view from below showing the portion of the arm of FIG. 8 without the electrode.

The electrodes 200 are slidably restrained to the arms, so as to allow to reach all the possible positions provided by the international standard 10/20, as well as of any other standard known in the field, synergistically with the adjustment of the position of the arms relative to the central portion 110. As shown in FIGS. 8 and 9 one or more slots along are formed each arm for this purpose. FIG. 8 e.g. shows a portion of the first arm 120 and a slot formed along it, which is schematically indicated with reference number 121.

Figure 10:
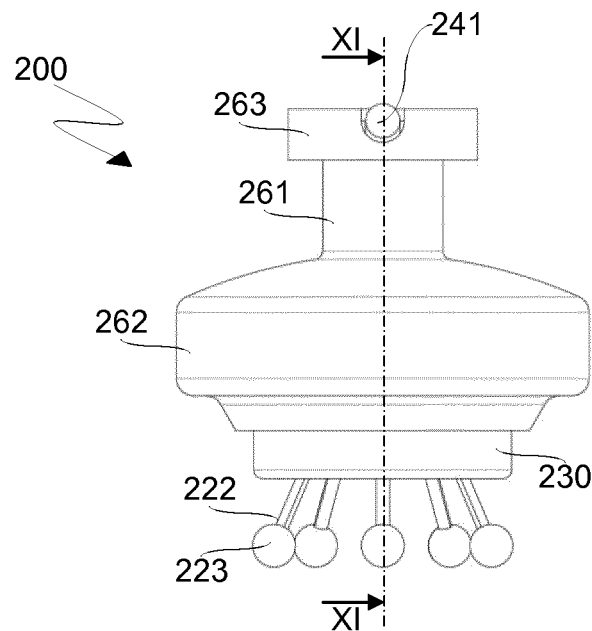
FIG. 10 is a front view showing an electrode of the portable device for video electroencephalography according to the present invention.
Figure 11:
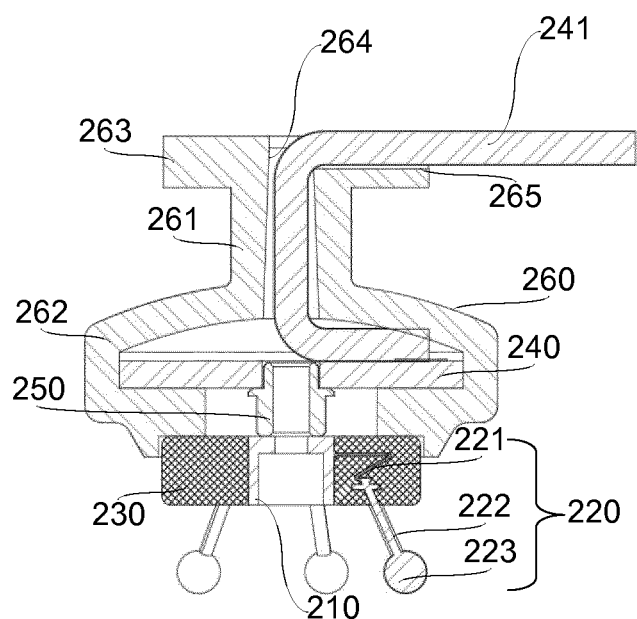
FIG. 11 is a longitudinal section view of the electrode of FIG. 10 taken along a plane passing through line XI-XI.

Now referring to FIGS. 10 and 11, each electrode 200 includes a mount 210, having for example a cylindrical shape, from which a plurality of arms 220 extend radially outwards, five arms in the example shown in the figures. The mount 210 and the arms 220 are made of a conductive metal material such as silver/gold. Each arm 220 includes a flexible portion 221 secured to the mount 210, for example in the form of a flap or of a wire made of a conductive metal material, and a rigid e.g. straight portion 222 restrained to the flexible portion 221, and a rounded portion 223 that is arranged at the free end of the rigid portion 222 and is therefore intended to contact a patient's scalp.

The arms 220 thus configured are partially embedded in a matrix 230 having an annular shape and made of a resilient polymeric material, such as silicone, which surrounds the mount 210. More particularly the flexible portions 221 of the arms 220 are fully embedded in the matrix 230, while the rigid portions 222 and the rounded end portions 223 protrude therefrom.

The mount 210, the arms 220 and the matrix 230 of resilient polymeric material together form the contact element of each electrode 200. It will be appreciated that, thanks to the combination between the flexible portions 221 of the arms 220 and the matrix 230 of resilient polymeric material, it is possible to obtain a high degree of deformability of the contact elements of the individual electrodes 200 both axially and laterally, which facilitates their penetration between a patient's hair, and hence their contact with the scalp.

It will also be appreciated that the high degree of deformability of the contact elements of the individual electrodes 200 minimizes the pain caused to a patient during an extended monitoring period, for example of the order of hours or even days, and improves the safety of the device in case of impacts or falls, encouraging this type of monitoring that is particularly useful for patients with epilepsy.

According to a preferred embodiment of the invention, the mount 210 and the flexible portions 221 of the arms 220 restrained thereto are realized as contact portions and electric tracks made of a conductive metallic material on a flexible support made of a plastic material, for example of polyimide, with which they define a flexible electronic circuit. This embodiment offers the advantage of more robust, simpler and cheaper structure at an industrial level, which may also be more easily fitted into the matrix 230.

The connection between the flexible portions 221 and the rigid portions 222 of the arms 200 can for example be achieved by fitting the ends of the flexible portions 221 bearing contact portions into corresponding slots formed in the rigid portions 222.

A printed circuit board 240 is restrained to the mount 210. The printed circuit board 240 comprises a plurality of electronic components (not shown) mounted thereon and required for the acquisition of bioelectrical signals, and a transmission cable 241 connected to an electronic control unit 300 of the control device 100 that is housed in the central portion 110. The printed circuit board 240 may be restrained to the mount 210 by way of a screw connection element 250 as shown in the illustrated example, or with technically equivalent connection means that are known to a skilled in the art.

The printed circuit board 240, the transmission cable 241 and the possible connection element 250 are accommodated in a casing 260 made of an insulating and resilient material, for example rubber or silicone, configured to slidably engage the slots formed in the arms of the device 100.

The casing 260, which has a substantially cylindrical shape, includes an intermediate portion 261 that has a reduced cross-section and forms a circumferential groove configured to allow fitting of the electrode 200 in the slots formed in the arms. The printed circuit board 240 is housed in a first portion 262 of the casing 260, while the transmission cable 241 protrudes therefrom at a second portion 263 of the casing 260 opposite to the first portion 262 with respect to the intermediate portion 261, for example through an axial channel 264 and a radial opening 265.

It will be appreciated that the contact element of the electrode 200 described above, and in particular the matrix 230 made of a resilient polymeric material which encloses the mount 210 and the arms 220, is outside the casing 260 thus closing the first portion 262 and separating and protecting the printed circuit board 240 arranged inside it and the related electric components.

The size of the intermediate portion 261 is larger than the width of the slots 121 formed in the arms of the device 100, such that mounting of the electrodes 200 is carried out by way of an interference fit between the casing 260 and the slots 121, which allows to maintain overtime the positions of the electrodes 200.

By exploiting the elasticity of the material of which the casing 260 is made, in order to move an electrode 200 along the respective slot is sufficient to pull it axially by grabbing the first and second portions 262, 263 of the casing 260. The intermediate portion 261 so pulled becomes thinner, thus allowing to temporarily remove the interference fit constraint with the slot 121.

Still with reference to FIGS. 8 and 9, according to a preferred embodiment of the invention, each slot 121 advantageously comprises a plurality of openings 122 having a size larger than the width of the slot 121 and defining a plurality of predefined locations for the correct positioning of the electrodes 200 along the arms, and therefore with respect to the patient's head, according to the provisions of the international standard 10/20. To this aim the openings 122 have a surface area substantially corresponding to the size of the intermediate portion 261 of the casing 260, thereby allowing to lock the electrodes 200 in place.

In the illustrated embodiment three openings 122 are e.g. shown having a circular shape and respectively formed at the ends and in the middle of the slots 121, which define a corresponding number of positions for an electrode 200.

In order to prevent the transmission cable 241 from entering the slot 121 or simply contacting the patient's head thus hindering the maneuver of the electrode 200, each slot 121 may be advantageously provided with a sealing lip 123 which keeps it closed where no electrode 200 is present. In the illustrated embodiment, the lip seal 123 is interrupted at the three openings 122.

According to a preferred embodiment, the arms 100 of the device are hollow, thus allowing to house and protect inside them the transmission cables 241 of the electrodes 200, as shown in FIGS. 8 and 9. Access to the transmission cables and to the electrodes is made possible by removable covers that are not shown in FIGS. 8 and 9.

Maintaining the position of the electrodes 200 in the respective arms can be further facilitated by fitting their second portion 263 in a slider 124 slidably movable along the cavity of the single arm. As shown in FIG. 8, the slider comprises a pair of pins 125 which engage respective notches 126 formed in the peripheral edge of the arm 120 in correspondence of each opening 122.

According to the present invention, the device 100 also comprises at least one supporting member 400 and at least one camera 500 mounted on the supporting member 400 and facing the helmet structure.

Referring again to FIGS. 1, 2 and 5, in the illustrated embodiment the supporting member 400 is for example made up of a pair of arms identical to each other, for example connected to the central portion 110 in a symmetrical position with respect to a sagittal plane. Each arm 400 includes, for example, a fixed portion 401 and a movable portion 402 restrained to the fixed portion 401, for example through a hinge 403. The movable portions 402 of the two arms 400 are both restrained to the camera 500 in correspondence of an attachment member 501 thereof.

According to a further aspect of the invention, the position of the camera 500 with respect to the supporting member 400, and thus relative to the helmet structure, may be adjusted by way of panning means operably connected to the video camera 500 and the supporting member 400, such as e.g. a micromotor and/or a kinematic chain that is controllable, preferably from remote, through the electronic central unit 300. The panning means of the camera 500 give a physician the possibility to adjust the position of the video camera 500 relative to the supporting member 400 so as to suitably frame the specific portions of the face of a patient during a monitoring period, thus helping to improve the accuracy of a diagnosis based on the video electroencephalography device 100.

The camera 500 is advantageously configured for both daytime and nighttime recording, for example by means of an infrared LED lighting system, in order to allow monitoring over periods of 24 hours or longer.

According to the invention, the device 100 may also advantageously comprise a microphone 600, which associates sound data to the video recordings, thus helping to improve the quality and completeness of the video-EEG monitoring and the accuracy of the diagnosis it allows to make.

In the illustrated embodiment, the microphone 600 is for example associated with the camera 500 and integrated in the casing that encloses its optics. This configuration is advantageous because the positioning of the camera 500 with respect to the patient's face at the same time determines the positioning of the microphone 600 in the same direction, thus allowing to acquire sounds coming from the patient, while excluding the possible noise and/or sounds surrounding him/her, which might alter acquisition and diagnosis. A possible position of the microphone 600 is schematically shown in the detail view of FIG. 3.

The bioelectric signals acquired from the electrodes 200, as well as the audio-video signals simultaneously obtained through the camera 500 and the microphone 600 are received by the electronic control unit 300. A microprocessor of the electronic control unit 300 is configured for the acquisition of bioelectric signals detected by the electrodes 200, simultaneously and in parallel, and is also configured to synchronize these signals with the video signals recorded by the camera 500, as well as any audio signal recorded by the microphone 600, thus offering the advantage of having data sets which together represent the brain's electrical activity at the same time and at all the contact points chosen by the physician and used to correlate this electrical activity to specific images and possibly also to sounds, which allows to carry out particularly effective diagnoses in patients with epilepsy and in some cases even allows to identify and predict a seizure.

The electronic control unit 300 may be advantageously provided with a removable storage medium such as an SD card (Secure Digital) for the recording and processing of video-EEG data on a separate processing device, such as a remote electronic unit such as an electronic calculator. In addition or alternatively to this, the data received may for example be transmitted to the remote electronic unit by resorting to the wireless technology.

The device of the invention may also be provided with further electronic components, such as a triaxial accelerometer useful to detect seizures, and a Hall effect sensor that can be used to power the device 100 in combination with a support wearable by a patient, a physician or, more generally, by medical personnel, such as a bracelet provided with a magnet. The Hall effect sensor may be also used to mark particular events during the monitoring period, thus allowing to identify specific parts of the EEG record and its related audio-video synchronous signals.

The electronic control unit 300 is powered by a battery, preferably of the rechargeable type in a wireless mode or, alternatively, through an electric cable, for example provided with a USB connector.

The present invention has hereto been described with reference to preferred embodiments thereof. It will be appreciated that there may be other embodiments relating to the same inventive idea as defined by the scope of protection of the claims set forth below.

As far as the electrodes of the portable device Video-EEG are concerned, separate protection may be requested regardless of the presence of a patient video recording system, and in particular also independently of the features of the independent claim 1.

The invention claimed is:

1. A portable device for video electroencephalography, said device comprising:
    a central portion;
    a plurality of arcuate arms directly connected to the central portion in a movable manner, wherein said arcuate arms together define a helmet structure adapted to be worn on the head of a patient;
    one or more electrodes, wherein each of said arcuate arms is configured to allow mounting of the one or more electrodes;
    an electronic central unit mounted on said helmet structure, wherein said one or more electrodes are connected to the electronic central unit;
    at least one supporting member; and
    at least one video camera mounted on said supporting member so as to face the helmet structure, said video camera being connected to said electronic central unit,
    wherein said arms comprise a first arm and a second arm which extend away from each other in a longitudinal direction (L), as well as a third arm and a fourth arm which extend away from each other in a front direction (F), wherein said first and second arms are pivotable on said central portion about respective axes parallel to said front direction (F), and said third and fourth arms are pivotable about respective axes parallel to said longitudinal direction (L).

2. A device according to claim 1, further comprising a microphone connected to the electronic central unit.

3. A device according to claim 2, further comprising a casing enclosing video optics components of the video camera, wherein said microphone is integrated in the casing.

4. A device according to claim 1, further comprising biasing means associated to the axes around which the first, second, third and fourth arms are pivotable on the central portion rotate, said biasing means being configured so as to urge toward one another the arms that are arranged opposite to each other relative to the central portion.

5. A device according to claim 1, wherein said arms further comprise a fifth arm and a sixth arm, which are respectively restrained at the ends of said third arm and extend therefrom away from each other in the longitudinal direction (L), as well as a seventh arm and an eighth arm, which are respectively restrained at the ends of said fourth arm and extend therefrom away from each other in the longitudinal direction (L).

6. A device according to claim 5, wherein said fifth, sixth, seventh and eighth arm are pivotable on the respective third and fourth arms about axes that are parallel to the front direction (F).

7. A device according to claim 6, wherein the fifth, sixth, seventh and eighth arm are pivotally mounted on the third arm and the fourth arm through respective clutch mechanisms.

8. A device according to claim 1, wherein the supporting member is restrained to the central portion and extends therefrom in the longitudinal direction (L).

9. A device according to claim 1, further comprising panning means operably connected with the video camera and the supporting member, said panning means being configured to adjust the position of the video camera relative to the supporting member.

10. A device according to claim 1, wherein said electrodes are dry electrodes and are slidably restrained to the arms along slots formed therein, and wherein each slot comprises a plurality of openings having a size larger than the width of the slot and defining a plurality of predefined locations for the positioning of the electrodes along the arms.

11. A device according to claim 10, wherein each electrode comprises a mount made of a conductive metal material and a plurality of arms extending therefrom radially outwards, said plurality of arms being made of a conductive metal material, the arms being partially embedded in a matrix having an annular shape and made of a resilient polymeric material, said matrix surrounding said mount.

12. A device according to claim 11, wherein each arm made of a conductive metal material includes a resilient portion restrained to said mount and a rigid portion restrained to said resilient portion, as well as a rounded portion arranged at the free end of said rigid portion.

13. A device according to claim 12, wherein the resilient portion is completely embedded in the matrix, while the rigid portion and the rounded portion protrude therefrom.

14. A device according to claim 12, wherein the mount and the resilient portions of the arms restrained thereto are formed on a flexible plastic substrate.

15. A device according to claim 11, wherein the mount of the electrode is connected to a printed circuit board on which a plurality of electronic components configured for the acquisition of bioelectrical signals and a transmission cable connected to the electronic central unit are mounted.

16. A device according to claim 15, wherein said printed circuit board and said transmission cable are housed in a casing made of an insulating, resilient material and are configured to be slidably fitted into slots formed in the arcuate arms.

17. A device according to claim 16, wherein said casing has a substantially cylindrical shape and comprises an intermediate portion of reduced cross-section configured to allow the electrode to fit into the slots formed in the arcuate arms, and wherein the printed circuit board is housed in a first portion of the casing, while the transmission cable protrudes therefrom through a second portion of the casing opposite to the first portion with respect to said intermediate portion.

18. A device according to claim 17, wherein the size of the reduced cross-section of the intermediate portion is larger than the width of the slots formed in the arcuate arms.

19. A device according to claim 18, wherein each of the slots formed in the arcuate arms comprises a plurality of openings the surface area of which substantially corresponds to the surface area of the cross-section of the intermediate portion of the casing.

* * * * *